(12) United States Patent
Inakoshi et al.

(10) Patent No.: US 7,652,052 B2
(45) Date of Patent: Jan. 26, 2010

(54) PROCESS FOR PRODUCING RAMOSETRON OR ITS SALT

(75) Inventors: Masatoshi Inakoshi, Tokyo (JP); Kiyotaka Marumo, Tokyo (JP); Noriya Yamamoto, Tokyo (JP); Hiroshi Kiyonaga, Tokyo (JP); Yasuaki Ohishi, Tokyo (JP)

(73) Assignee: Astellas Pharma Inc., Tokyo (JP)

( * ) Notice: Subject to any disclaimer, the term of this patent is extended or adjusted under 35 U.S.C. 154(b) by 113 days.

(21) Appl. No.: 11/918,282

(22) PCT Filed: Apr. 10, 2006

(86) PCT No.: PCT/JP2006/307543

§ 371 (c)(1),
(2), (4) Date: Oct. 11, 2007

(87) PCT Pub. No.: WO2006/109762

PCT Pub. Date: Oct. 19, 2006

(65) Prior Publication Data

US 2009/0069570 A1    Mar. 12, 2009

(30) Foreign Application Priority Data

Apr. 11, 2005  (JP) .............................. 2005-113061

(51) Int. Cl.
*A61K 31/416*   (2006.01)
*C07D 231/56*   (2006.01)

(52) U.S. Cl. .................... 514/394; 548/302.7
(58) Field of Classification Search .............. 548/302.7; 514/394
See application file for complete search history.

(56) References Cited

FOREIGN PATENT DOCUMENTS

| CN | 1696128 A | 11/2005 |
|----|-----------|---------|
| CN | 1765896 A | 5/2006 |
| EP | 0 381 422 A1 | 8/1990 |
| EP | 381422 A1 * | 8/1990 |
| JP | 06-25153 | 4/1994 |
| WO | WO 01/36498 A1 | 5/2001 |

OTHER PUBLICATIONS

Olah; "Catalysts and Solvents", Friedel-Crafts and Related Reactions, vol. 1, General Aspects, Table XLIV, pp. 312-315, (1963).
Olah; "Catalysts and Solvents", Friedel-Crafts and Related Reactions, vol. 1, General Aspects, Table XLIV, pp. 312-315.
Ohta et al.; "Novel 5-Hydroxytryptamine (5-HT$_3$) Receptor Antagonists. III.[1)] Pharmacological Evaluations and Molecular Modeling Studies of Optically Active 4,5,6,7-Tetrahydro-1*H*-Benzimidazole Derivatives", Chem. Pharm. Bull., vol. 44, No. 9, pp. 1707-1716, (1996).
"YM060, 5-HT$_3$ Receptor Antagonists", Drugs of the Future, Prous Science, vol. 17, No. 1, pp. 28-29, (1992).
Kiichi et al.; "Synthesis of 5-HT$_3$, Receptor Antagonists, [$^{11}$C]Y-25130 and [$^{11}$C]YM060", Appl. Radiat. Isot., vol. 46, No. 9, pp. 907-910, (1995).

* cited by examiner

*Primary Examiner*—Kamal A Saeed
*Assistant Examiner*—Janet L Coppins
(74) *Attorney, Agent, or Firm*—Finnegan, Henderson, Farabow, Garrett & Dunner, L.L.P.

(57) ABSTRACT

To provide a novel process for producing ramosetron or its salt that is useful as a pharmaceutical, especially as a therapeutic and/or preventive agent for digestive symptoms caused by administration of an anti-malignant tumor agent, diarrheal-type irritable bowel syndrome, diarrheal symptoms of irritable bowel syndrome, etc.

Ramosetron or its salt can be produced by reacting a compound of the formula (I):

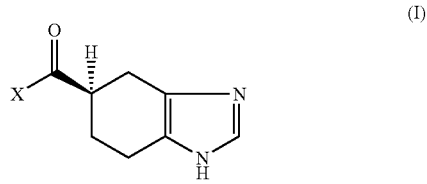

(I)

[wherein X is a halogen] or a salt thereof with 1-methyl-1H-indole in the presence of a Lewis acid selected from the group consisting of a lower alkylaluminum dihalide, a di-lower alkylaluminum halide, a tri-lower alkylaluminum and a lower alkylaluminum sesquihalide.

6 Claims, No Drawings

PROCESS FOR PRODUCING RAMOSETRON OR ITS SALT

TECHNICAL FIELD

The present invention relates to a novel process for producing ramosetron or a salt thereof that is useful as a pharmaceutical, especially as a 5-HT$_3$ receptor antagonist, more specifically, a therapeutic agent and/or preventive agent for digestive symptoms (nausea, emesis) caused by administration of an anti-malignant tumor agent (cisplatin or the like), diarrheal-type irritable bowel syndrome, diarrheal symptoms of irritable bowel syndrome, and the like.

BACKGROUND OF THE INVENTION

The chemical name of ramosetron is (−)-(R)-5-[(1-methyl-1H-indol-3-yl)carbonyl]-4,5,6,7-tetrahydro-1H-benzimidazole, and it has the structure represented by the formula (II).

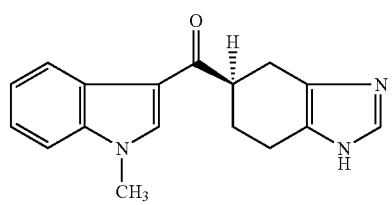

(II)

It is known that ramosetron or a salt thereof has a potent 5-HT$_3$ receptor antagonism (Patent Reference 1, Non-patent references 1 and 2), and it is on the market as a preventive or therapeutic agent for digestive symptoms (nausea, emesis) caused by administration of an anti-malignant tumor agent (cisplatin or the like). In addition, a possibility has been reported that ramosetron or a salt thereof may be useful as an agent for treating diarrheal-type irritable bowel syndrome or an agent for improving diarrheal symptoms of irritable bowel syndrome (Patent Reference 1), and its clinical trials are now in progress as an agent for treating diarrheal-type irritable bowel syndrome or an agent for improving diarrheal symptoms of irritable bowel syndrome.

As a process for producing ramosetron or a salt thereof, the following production methods are known.

Patent Reference 1 describes a production method shown by the following Production method A, namely a method for producing a tetrahydrobenzimidazole derivative (V) by allowing a heterocyclic compound (III) to react with a carboxylic acid represented by a formula (IV) or its reactive derivative.

(Production Method A)

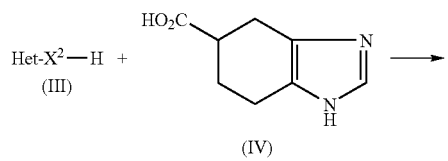

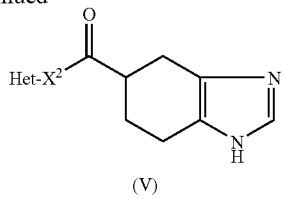

(V)

(In the formula, X$^2$ is a single bond and binds to a carbon atom on the heterocyclic ring represented by Het.)

As an illustrative production method of ramosetron, Patent Reference 1 describes a production method (Production method A-1) in which racemic ramosetron are obtained by using 1-methyl-1H-indole as the compound (III), and N,N-diethyl-4,5,6,7-tetrahydrobenzimidazole-5-carboxamide or N-[(4,5,6,7-tetrahydrobenzimidazol-5-yl)carbonyl]pyrrolidine, which are acid amides, as the reactive derivative of compound (IV), and allowing them to undergo treatment with phosphorus oxychloride (Vilsmeyer reaction), and then their optical resolution is carried out by fractional crystallization using (+)-dibenzoyltartaric acid.

In addition, the Patent Reference 1 exemplifies an acid halide as one of the reactive derivatives of the compound (IV), and also describes another production method of the compound (V) (Production method A-2) in which the heterocyclic compound (III) is condensed with an acid halide of the compound (IV) by the Friedel-Crafts acylation reaction using a Lewis acid as the catalyst. However, illustrative production example of ramosetron by the Friedel-Crafts acylation reaction is not described therein.

Also, a method similar to the Production example A-1 is described in Non-patent References 1 and 2 as a production method of ramosetron.

In addition, Non-patent Reference 3 describes a method for producing ramosetron labeled with $^{11}$C, represented by a Production method B. However, it discloses only the methylation step, and does not disclose a production method of nor-YM060 as the starting material.

(Production Method B)

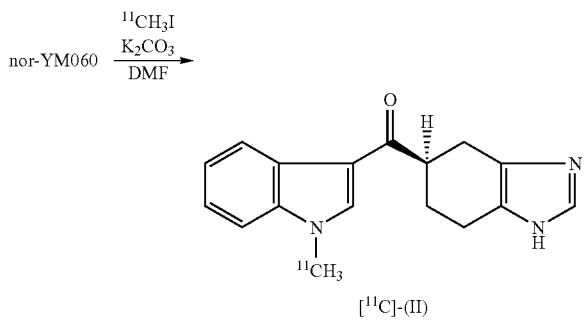

(In the formula, nor-YM060 means (R)-5-[(1H-indol-3-yl)carbonyl]-4,5,6,7-tetrahydro-1H-benzimidazole which was provided by the present applicant, DMF means dimethylformamide.)

Non-patent Reference 1: *Chemical & Pharmaceutical Bulletin,* 1996, vol. 44, no. 9, p. 1707-1716

Non-patent Reference 2: *Drugs of the Future,* 1992, vol. 17, no. 1, p. 28-29

Non-patent Reference 3: *Applied Radiation and Isotopes*, 1995, vol. 46, no. 9, p. 907-910
Patent Reference 1: JP-B-6-25153

DISCLOSURE OF THE INVENTION

Problems that the Invention is to Solve

The conventional production methods of ramosetron are not industrially-satisfactory in terms of the production efficiency. Accordingly, great interests have been directed toward the development of an efficient method for producing ramosetron or a salt thereof, particularly a method for producing ramosetron which does not cause racemization and can keep the optical purity.

Means for Solving the Problems

The present inventors have conducted extensive studies with the aim of developing an industrially more efficient production method of ramosetron or a salt thereof. As a result, it was found that, according to the following production method, ramosetron or a salt thereof may be produced with high efficiency through progress of the reaction which hardly reduce its optical purity and may keep its stereochemistry, thereby accomplishing the present invention.

That is, according to the present invention, the novel production methods of ramosetron or a salt thereof shown in the following are provided.

(1) (Production Method 1)

A method for producing ramosetron or a salt thereof, characterized in that a compound represented by a formula (I)

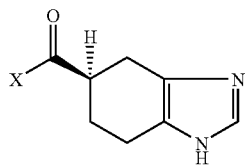

(I)

[X in the formula represents a halogen]

or a salt thereof is allowed to react with 1-methyl-1H-indole in the presence of a Lewis acid selected from the group consisting of a lower alkylaluminum dihalide, a di-lower alkylaluminum halide, a tri-lower alkylaluminum, and a lower alkylaluminum sesquihalide.

(2) (Production Method 2)

A method for producing ramosetron or a salt thereof, characterized in that a compound represented by the formula (I) described in (1) is prepared by allowing (R)-4,5,6,7-tetrahydro-1H-benzimidazole-5-carboxylic acid or a salt thereof to react with a halogenation agent, and then allowed to react with 1-methyl-1H-indole in the presence of a Lewis acid selected from the group consisting of a lower alkylaluminum dihalide, a di-lower alkylaluminum halide, a tri-lower alkylaluminum, and a lower alkylaluminum sesquihalide.

(3) The production method described in (1) or (2), wherein the Lewis acid is diethylaluminum chloride or diethylaluminum sesquichloride.

(4) The production method described in (3), wherein solvent of the reaction is an aromatic hydrocarbon.

(5) The production method described in (4), wherein the aromatic hydrocarbon is toluene.

(6) Ramosetron or a salt thereof produced by the production method described in (1).

(7) Ramosetron or a salt thereof produced by the production method described in (2).

In addition, according to the present invention, the composition shown below, which comprises ramosetron or a salt thereof, is also provided.

(8) A composition which comprises ramosetron or a salt thereof, characterized in that it contains 5-[(1-methyl-1H-indol-5-yl)carbonyl]-4,5,6,7-tetrahydro-1H-benzimidazole or a salt thereof and/or 5-[(1-methyl-1H-indol-6-yl)carbonyl]-4,5,6,7-tetrahydro-1H-benzimidazole or a salt thereof, in a total amount of less than 1% based on ramosetron or a salt thereof.

ADVANTAGE OF THE INVENTION

Since the reaction in the production method of the present invention progresses by keeping the stereochemistry, as is described later, ramosetron or a salt thereof having a high optical purity may be produced with a high yield from (R)-4,5,6,7-tetrahydro-1H-benzimidazole-5-carboxylic acid or a salt thereof which is conventionally known and may be produced easily.

On the other hand, in the production method A-1 described in the Patent Reference 1, ramosetron is produced by condensing an acid amide compound and 1-methyl-1H-indole by the Vilsmeyer reaction and then carrying out optical resolution by fractional crystallization using (+)-dibenzoyltartaric acid. However, when the optical resolution is arranged at the after step of the production process, it becomes necessary to excessively use the material for the production of the unnecessary optical isomer which occupies the half part. However, even when an optically active acid amide compound is used as the starting material in the production method A-1, it is completely racemized at the step of Vilsmeyer reaction, so that it becomes necessary to carry out a treatment for increasing the optical purity after the reaction in order to obtain ramosetron having a high optical purity. On the other hand, according to the method of the present invention, the reaction progresses with a high yield while keeping the stereochemistry, so that ramosetron having a high optical purity can be produced from the optically active compound (I) industrially efficiently. In addition, 1,2-dichloroethane is used in the production method A-1 as the solvent at the step of Vilsmeyer reaction, but it is considered now that it should not be used in the production of pharmaceutical preparations. On the other hand, toluene is suitably used in the production method of the present invention. In addition, in the production of ramosetron hydrochloride actually produced by the applicant by the production method A-1, crystals containing ramosetron are filtered 6 times in total in the steps of taking out and purifying racemic bodies of ramosetron, ramosetron (+)-dibenzoyltartarate and ramosetron hydrochloride, for the purpose of obtaining ramosetron hydrochloride having a high optical purity. On the other hand, as is described later, ramosetron hydrochloride having a high optical purity may be obtained by the production method of the present invention through once, or twice including its purification, of filtration, so that the handing is convenient.

Also, the production method A-2 is a method for producing a tetrahydrobenzimidazole derivative (V) by allowing a heterocyclic compound (III) and an acid halide of the compound (IV) to undergo Friedel-Crafts acylation reaction using a Lewis acid as the catalyst. However, as described in the foregoing, an illustrative production example of ramosetron by this production method is not described therein. Also, the Patent Reference 1 describes, as a production example of analogous compounds, a method for producing 5-[(benzothiophene-3-yl)carbonyl]-4,5,6,7-tetrahydrobenzimidazole and 5-[(2-methylbenzofuran-3-yl)carbonyl]-4,5,6,7-tetrahydrobenzimidazole by Friedel-Crafts acylation reaction respectively using aluminum chloride and tin tetrachloride as the Lewis acid, but it cannot be said that their yields are suitable. In addition, when the same reaction conditions were applied to the production of ramosetron, the yield was also low, and its purification was difficult to carry out due to the by-production of a tarry highly viscous substance. Thus, it was not able to industrially use Lewis acids which are generally and frequently used in the production of ramosetron. Accordingly, the present inventors have extensively examined on Lewis acids and, as a result, unexpectedly found that ramosetron can be produced with less by-products and high yield when a lower alkylaluminum dihalide, a di-lower alkylaluminum halide, a tri-lower alkylaluminum and a lower alkylaluminum sesquihalide were used as Lewis acids. In addition, in the case of the production of ramosetron using the Lewis acids to be used in the present invention, it was revealed unexpectedly that the reaction progresses by hardly reducing the optical purity while keeping the stereochemistry when the reaction is carried out using the optically active compound (I). Based on this, according to the production method of the present invention, ramosetron having a high optical purity can be produced industrially efficiently from the optically active compound (I).

In addition, labeled ramosetron is produced in the production method B, by the methylation of an optically active compound (V) with labeled methyl iodide. However, the production method B is a production method which requires nor-YM060 in order to label the 1-position of indol, so that the process becomes longer than the ramosetron production method, by a factor of 1 step. On the other hand, according to the present invention, the number of steps becomes short because the production does not require nor-YM060.

Accordingly, the production method of the present invention is a superior production method in comparison with the conventional production methods, in terms of (1) high yield, (2) avoidance of the use of solvents which should not be used in producing pharmaceutical preparations, (2) less environmental loading, (3) shortened number of total steps and (4) improved convenience of the handling.

BEST MODE FOR CARRYING OUT THE INVENTION

Further description on the present invention is as follows.

In this description, "alkyl" means a straight or branched saturated aliphatic hydrocarbon chain.

The "lower alkyl" means a $C_{1-6}$ alkyl. Illustrative examples include methyl, ethyl, propyl, butyl, pentyl, hexyl, isopropyl, tert-butyl and the like. Methyl and ethyl are preferable.

The "halogen" means F, Cl, Br and I. Cl is preferable.

The "tri-lower alkylaluminum" means a compound represented by Al(lower alkyl)$_3$. Illustrative examples include trimethylaluminum, triethylaluminum and triisobutylaluminum. Trimethylaluminum is preferable.

The "lower alkylaluminum dihalide" means a compound represented by Al(lower alkyl)(halogen)$_2$. Illustrative examples include methylaluminum dichloride and ethylaluminum dichloride. Ethylaluminum dichloride is preferable.

The "di-lower alkylaluminum halide" means a compound represented by Al(lower alkyl)$_2$(halogen). Illustrative examples include dimethylaluminum chloride and diethylaluminum chloride. Diethylaluminum chloride is preferable.

The "lower alkylaluminum sesquihalide" means a compound represented by Al$_2$(lower alkyl)$_3$(halogen)$_3$. Illustrative examples include methylaluminum sesquichloride and ethylaluminum sesquichloride. Ethylaluminum sesquichloride is preferable.

The "aromatic hydrocarbon" as the solvent for the Friedel-Crafts acylation reaction may be any substance which may be used as the solvent for Friedel-Crafts acylation reaction. Illustrative examples thereof include benzene, toluene, xylene, mesitylene, chlorobenzene, dichlorobenzene and nitrobenzene. Toluene is preferable.

The "salt thereof" in the "ramosetron or a salt thereof" may be any substance which is a salt of ramosetron with a pharmaceutically acceptable acid. Illustrative examples thereof include an acid addition salt of ramosetron with inorganic acid such as hydrochloric acid, sulfuric acid or the like or with an organic acid such as acetic acid, oxalic acid, malonic acid, succinic acid or the like. As the "ramosetron or a salt thereof", ramosetron or ramosetron chloride are preferable. A generally used salt formation method may be used in the salt formation.

In addition, the present invention also includes a method for producing a compound, so-called labeled substance, in which a part or all of the atoms constituting ramosetron and/or a production material thereof are replaced by a radioactive isotope.

The production method 1 of the present invention is a ramosetron production method in which the compound represented by the formula (I) and 1-methyl-1H-indole are allowed to undergo the Friedel-Crafts acylation reaction in the presence of a Lewis acid while keeping the stereochemistry.

The reaction may be carried out using said production material on an equimolar basis or one of them in an excess amount under cooling to heating, wherein it is preferable to carry out it under cooling.

As to the solvent to be used in the reaction, no solvent may be used or a solvent inert to the reaction may be used, including aromatic hydrocarbons such as benzene, toluene, xylene, mesitylene and the like, ethers such as diethyl ether, tetrahydrofuran, dimethoxyethane (DME) and the like, halogenated hydrocarbons such as dichloromethane, 1,2-dichloroethane, chloroform and the like, acetonitrile, dimethyl sulfoxide (DMSO), ethyl acetate, N,N-dimethylformamide (DMF), nitromethane, carbon disulfide and the like, as well as a mixed solvent thereof. Aromatic hydrocarbons are preferable and toluene is more preferable.

The Lewis acid may be used in an equivalent or excess amount, and is preferably diethylaluminum chloride or ethylaluminum sesquichloride.

In addition, Cl is preferable as the X in the formula (I).

The production method 2 of the present invention is a ramosetron production method in which (R)-4,5,6,7-tetrahydro-1H-benzimidazole-5-carboxylic acid or a salt thereof is allowed to react with a halogenation agent to obtain the compound represented by the formula (I), and then this and 1-methyl-1H-indole are allowed to undergo the Friedel-Crafts acylation reaction in the presence of a Lewis acid while keeping stereochemistry.

The first half halogenation reaction may be carried out using said production material on an equimolar basis or one of them in an excess amount under cooling to heating under reflux, wherein it is preferable to carry out it under heating.

The reaction may be carried out without solvent or in a solvent inert to the reaction, including an aromatic hydrocarbon such as benzene, toluene, xylene, mesitylene and the like, an ether such as diethyl ether, tetrahydrofuran, dimethoxyethane (DME) and the like, a halogenated hydrocarbon such as dichloromethane, 1,2-dichloroethane, chloroform and the like, acetonitrile, ethyl acetate, N,N-dimethylformamide (DMF) and the like, or in a mixed solvent thereof. Tetrahydrofuran and dimethoxyethane are preferable.

As the halogenation agent, halogenation agents generally used in the production of acid halides, such as thionyl chloride, oxalyl chloride, phosphorus pentachloride, thionyl bromide, phosphorous tribromide and the like, may be used. Thionyl chloride is preferable.

In addition, Cl is preferable as the X in the formula (I).

Regarding the latter half Friedel-Crafts acylation reaction, the reaction may be carried out by the same method of the production method 1.

The acid halide produced in the first half step may be used in the latter half step by isolating or not isolating it.

According to the aforementioned production method 1 or production method 2, a composition which comprises ramosetron or a salt thereof, wherein it contains 5-[(1-methyl-1H-indol-5-yl)carbonyl]-4,5,6,7-tetrahydro-1H-benzimidazole (hereinafter "compound A") or a salt thereof and 5-[(1-methyl-1H-indol-6-yl)carbonyl]-4,5,6,7-tetrahydro-1H-benzimidazole "compound B" or a salt thereof, in a total amount of less than 1% based on ramosetron or a salt thereof can be obtained. Percent content of the compound A or a salt thereof and the compound B or a salt thereof based oh ramosetron or a salt thereof is preferably less than 0.5%, more preferably less than 0.2%, further preferably less than 0.1%, based on ramosetron or a salt thereof. The composition obtained in this manner, which comprises ramosetron or a salt thereof, may be used as a therapeutic agent and/or preventive agent for digestive symptoms (nausea, emesis) caused by administration of an anti-malignant tumor agent (cisplatin or the like), diarrheal-type irritable bowel syndrome, diarrheal symptoms of irritable bowel syndrome and the like.

Structures of the compound A and compound B are shown below.

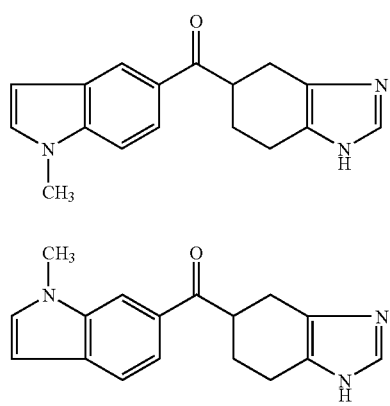

Compound A

Compound B

EXAMPLES

The following illustratively describes the present invention based on examples, but the invention is not restricted by these examples.

Example 1

By heating a mixture of 4.05 g of (R)-4,5,6,7-tetrahydro-1H-benzimidazole-5-carboxylic acid monohydrochloride (99.4% e.e.), 120 ml of dimethoxyethane and 5.47 g of thionyl chloride at 70° C. for 2 hours, (R)-4,5,6,7-tetrahydro-1H-benzimidazole-5-carbonyl chloride was synthesized, and the solvent was evaporated under a reduced pressure. A 80 ml portion of toluene was added to the residue and again evaporated under a reduced pressure, and the residue was mixed with 120 ml of toluene and 5.24 g of 1-methyl-1H-indole and cooled to −40° C. in an atmosphere of nitrogen. A 30 ml portion of 1.0 mol/l toluene solution of ethylaluminum sesquichloride was slowly added to this liquid and stirred at −40° C. for 3 hours, and 10 ml of tetrahydrofuran was added thereto after the stirring. This liquid was slowly dispersed in 160 ml of water cooled at 0° C., and after removing the organic layer, the water layer was washed with 40 ml of toluene and extracted by adding 80 ml of 2-butanone and 50 ml of 20% sodium hydroxide aqueous solution thereto. The water layer was washed with 40 ml of 2-butanone, and the organic layers were combined and washed twice with 20 ml of 10% brine and then with 4 ml of water. A 40 ml portion of ethanol was added to the thus obtained organic layer and evaporated under a reduced pressure, and 40 ml of ethanol was again added to the residue and evaporated under a reduced pressure. A 120 ml portion of a mixed solvent of ethanol and ethyl acetate (1:3) was added to the residue, and this was heated at 70° C. for 1 hour by adding 5 ml ethyl acetate solution of 4 mol/l hydrogen chloride and then slowly cooled to 0° C. The precipitated crystals were filtered, and the crystals were washed with an ethanol-ethyl acetate mixed solvent and then dried in vacuo at 50° C., thereby obtaining 4.98 g of (−)-(R)-5-[(1-methyl-1H-indol-3-yl)carbonyl]-4,5,6,7-tetrahydro-1H-benzimidazole monohydrochloride (yield 78.8%, 99.5% e.e.). FAB-MS (m/z): 280 [M+H$^+$]

$^1$H NMR (DMSO-$d_6$, 30° C.): δ ppm (TMS internal standard): 1.82-1.95 (1H, m), 2.12-2.22 (1H, m), 2.66-2.94 (4H, m), 3.63-3.72 (1H, m), 3.88 (3H, s), 7.24 (1H, t, J=8.0 Hz), 7.30 (1H, t, J=8.0 Hz), 7.56 (1H, d, J=8.0 Hz), 8.22 (1H, d, J=8.0 Hz), 8.53 (1H, s), 8.90 (1H, s), 14.42 (1H, br)

Example 2

By heating a mixture of 4.05 g of (R)-4,5,6,7-tetrahydro-1H-benzimidazole-5-carboxylic acid monohydrochloride (99.4% e.e.), 120 ml of dimethoxyethane and 5.47 g of thionyl chloride at 70° C. for 2 hours, (R)-4,5,6,7-tetrahydro-1H-benzimidazole-5-carbonyl chloride was synthesized, and the solvent was evaporated under a reduced pressure. A 80 ml portion of toluene was added to the residue and again evaporated under a reduced pressure, and the residue was mixed with 120 ml of toluene and 5.24 g of 1-methyl-1H-indole and cooled to −25° C. in an atmosphere of nitrogen. A 33 ml portion of 1.8 mol/l toluene solution of diethylaluminum chloride was slowly added to this liquid and stirred at −25° C. for 2 hours, and 8 ml of tetrahydrofuran was added thereto after the stirring. This liquid was slowly dispersed in 100 ml of water which was cooled at 0° C., and then heated to 45° C. After removing the organic layer, the water layer was washed with 40 ml of toluene, and this was extracted by adding 80 ml of 2-butanone and 50 ml of 20% sodium hydroxide aqueous solution thereto. The water layer was washed with 40 ml of 2-butanone, and the organic layers were combined and washed twice with 20 ml of 10% brine and then with 4 ml of water. The thus obtained organic layer was evaporated under a reduced pressure, 40 ml of ethanol was added to the resulting residue and evaporated under a reduced pressure, and 40 ml of ethanol was again added to the residue and evaporated under a reduced pressure. A 120 ml portion of a mixed solvent of ethanol and ethyl acetate (1:3) was added to the residue, and this was heated at 70° C. for 12 hours by adding 5 ml ethyl acetate solution of 4 mol/l hydrogen chloride and then slowly cooled to 0° C. The precipitated crystals were filtered, and the crystals were washed with an ethanol-ethyl acetate mixed solvent and then dried in vacuo at 50° C., thereby obtaining 5.45 g of (−)-(R)-5-[(1-methyl-1H-indol-3-yl)carbonyl]-4,5,6,7-tetrahydro-1H-benzimidazole monohydrochloride (yield 86.3%, 99.2% e.e.). FAB-MS (m/z): 280 [M+H⁺]

¹H NMR (DMSO-$d_6$, 30° C.): δ ppm (TMS internal standard): 1.82-1.95 (1H, m), 2.12-2.22 (1H, m), 2.66-2.94 (4H, m), 3.63-3.72 (1H, m), 3.88 (3H, s), 7.24 (1H, t, J=8.0 Hz), 7.30 (1H, t, J=8.0 Hz), 7.56 (1H, d, J=8.0 Hz), 8.21 (1H, d, J=8.0 Hz), 8.53 (1H, s), 8.91 (1H, s), 14.45 (1H, br)

The percentage content of the compound A and compound B, when ramosetron in the ramosetron-containing composition obtained in Example 1 or Example 2 was regarded as 100%, are shown in Table 1. In this connection, determination of the compound A and compound B was carried out by a liquid chromatography under the following conditions, and the peak area was measured by an automatic integration method.

Percentage content(%) of each compound=$A/B$

[In the formula, A represents the peak area of each compound in the sample, and B the peak area of ramosetron.]

<Test Conditions>

Detector: An ultraviolet absorption detector (measuring wavelength 254 nm)

Column: Nomura Kagaku Develosil C8-5 mm ID×150 mm

Column temperature: constant temperature at around 40° C.

Mobile Phase: 0.05 M $KH_2PO_4$ aqueous solution adjusted to pH 4.0 with $H_3PO_4$):MeOH:THF=8:1:1

Flow rate: 0.82 ml/min

When measured under the above conditions, retention times of ramosetron, compound A and compound B were about 7.41 minutes, about 9.45 minutes and about 11.91 minutes, respectively in Example 1, and about 7.01 minutes, about 9.00 minutes and about 12.46 minutes in Example 2.

TABLE 1

| Percentage content (%) of each compound | | |
|---|---|---|
| | Example 1 | Example 2 |
| Compound A | 0.04 | 0.63 |
| Compound B | 0.02 | 0.35 |

Physical property values of compound A and compound B are shown below.

Compound A:
LC-ESI: 280 [M+H⁺]
¹H-NMR (DMSO-$d_6$, 30° C.): δ ppm (TMS internal standard): 1.70-1.83 (1H, m), 2.05-2.14 (1H, m), 2.49-2.76 (4H, m), 3.84 (3H, s), 3.86-3.93 (1H, m), 6.61 (1H, d, J=3.1 Hz), 7.43 (1H, s), 7.44 (1H, d, J=3.1 Hz), 7.54 (1H, d, J=8.9 Hz), 7.83 (1H, d, J=8.9 Hz), 8.36 (1H, s)

Compound B:
LC-ESI: 280 [M+H⁺]
¹H-NMR (DMSO-$d_6$, 30° C.): δ ppm (TMS internal standard): 1.72-1.83 (1H, m), 2.05-2.12 (1H, m), 2.52-2.78 (4H, m), 3.89 (3H, s), 3.93-4.03 (1H, m), 6.52 (1H, d, J=3.1 Hz), 7.43 (1H, s), 7.57 (1H, d, J=3.1 Hz), 7.64 (1H, d, J=8.2 Hz), 7.70 (1H, dd, J=8.2 Hz, J=1.2 Hz), 8.20 (1H, s)

INDUSTRIAL APPLICABILITY

According to the production method of the present invention as described in the above, the reaction progresses by keeping the stereochemistry, so that ramosetron or a salt thereof having a high optical purity can be produced with high yield from (R)-4,5,6,7-tetrahydro-1H-benzimidazole-5-carboxylic acid or a salt thereof which can be produced easily. In addition, the composition which comprises ramosetron or a salt thereof, obtained by the aforementioned production method, can be used as a therapeutic agent and/or preventive agent for digestive symptoms (nausea, emesis) caused by administration of an anti-malignant tumor agent (cisplatin or the like), diarrheal-type irritable bowel syndrome, diarrheal symptoms of irritable bowel syndrome and the like.

The invention claimed is:

1. A method for producing ramosetron or a salt thereof, characterized in that a compound represented by a formula (I)

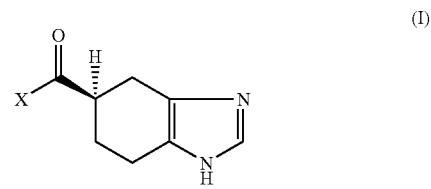

(I)

[the sign in the formula has the following meaning, X: a halogen]
or a salt thereof is allowed to react with 1-methyl-1H-indole in the presence of a Lewis acid selected from the group consisting of a lower alkylaluminum dihalide, a di-lower alkylaluminum halide, a tri-lower alkylaluminum and a lower alkylaluminum sesquihalide.

2. A method for producing ramosetron or a salt thereof, characterized in that a compound represented by the formula (I) described in claim 1 is prepared by allowing (R)-4,5,6,7-tetrahydro-1H-benzimidazole-5-carboxylic acid or a salt thereof to react with a halogenation agent, and then it is allowed to react with 1-methyl-1H-indole in the presence of Lewis acid selected from the group consisting of a lower alkylaluminum dihalide, a di-lower alkylaluminum halide, a tri-lower alkylaluminum and a lower alkylaluminum sesquihalide.

3. The production method described in claim 1 or 2, wherein the Lewis acid Is diethylaluminum chloride or ethylaluminum sesquichloride.

4. The production method described in claim 3, wherein solvent of the reaction is an aromatic hydrocarbon.

5. The production method described in claim 4, wherein the aromatic hydrocarbon is toluene.

6. A composition which comprises ramosetron or a salt thereof, characterized in that it contains 5-[(1-methyl-1H-indol-5-yl)carbonyl]-4,5,6,7-tetrahydro-1H-benzimidazole or a salt thereof and/or 5-[(1-methyl-1H-indol-6-yl)carbonyl]-4,5,6,7-tetrahydro-1H-benzimidazole or a salt thereof, in a total amount of less than 1% based on ramosetron or a salt thereof.

* * * * *